United States Patent [19]

Pappas

[11] Patent Number: 5,556,418
[45] Date of Patent: Sep. 17, 1996

[54] METHOD AND APPARATUS FOR PULSED MAGNETIC INDUCTION

[76] Inventor: Panagiotis T. Pappas, 13900 Panay Way, Marina Del Rey, Calif. 90292

[21] Appl. No.: 87,911

[22] Filed: Jul. 6, 1993

[51] Int. Cl.6 .................................................... A61N 1/00
[52] U.S. Cl. .................... 607/1; 607/71; 600/13
[58] Field of Search .................. 607/1, 2, 71; 600/9, 600/10, 13, 14; 315/111.21, 111.41, 111.91; 361/232, 233, 229; 313/231, 61, 4

[56] References Cited

U.S. PATENT DOCUMENTS

| | | | |
|---|---|---|---|
| 4,369,345 | 1/1983 | Czerlinski | 600/14 |
| 4,622,953 | 11/1986 | Gordon | 600/13 |
| 5,160,591 | 11/1992 | Liboff et al. | 600/13 X |

*Primary Examiner*—George Manuel
*Assistant Examiner*—Jeffrey R. Jastrzab
*Attorney, Agent, or Firm*—Robert M. Sperry

[57] ABSTRACT

An improved method and apparatus for pulsed magnetic induction by creating a plasma, supplying energy to excite said plasma to oscillate, and applying said the resulting oscillations to a patient or biological matter.

17 Claims, 2 Drawing Sheets

METHOD AND APPARATUS FOR PULSED MAGNETIC INDUCTION

RELATED CASES

This invention corresponds to that disclosed in my Greek patent application Ser. No. 920200309, filed Jul. 10, 1992, and now pending.

FIELD OF INVENTION

This invention relates to pulsed magnetic induction and is particularly directed to improved methods and apparatus for inducing electrical activity within and around the cells of the human body and other biological matter for therapeutic purposes and the like.

PRIOR ART

It has long been known that electrical current and electrical and magnetic fields have significant effects on the human body and various therapeutic techniques have been proposed heretofore for employing such electrical and magnetic effects to achieve beneficial results. In connection with this, it has been determined that human body cells have an electric potential across the surrounding membrane of the cell which energizes the sodium-potassium activity of the cell which, in turn, is responsible for the ion concentration of the cell and the maintenance of the transmembrane potential. When young and healthy, human body cells have a transmembrane potential of the order of 70 millivolts, whereas the transmembrane potential of an aged or unhealthy cell is considerably lower, approximately 50 millivolts. A cancer tumor cell can have a transmembrane potential as low as 15 millivolts. It has been found that cells with a low transmembrane potential are the source of pain generation signals which cause a sense of strong pain. At the same time, the membrane serves to resist extremely strong external electrical fields of the order at least of 70 mv/membrane thickness =70 mv/several Angstrom, which is of the order at least of $10^6$ v/m. Only a stronger external electrical source might serve to alter directly the transmembrane potential and, hence, effect the health of the cell. The value of $10^6$ v/m for an applied electrical field is prohibitive, as it surpasses the dielectric strength of the atmospheric air, which is 10 Kv/cm, or just $10^6$ v/m, i.e. the atmospheric air will break down by such a strong electric field before the membrane of a cell breaks down. This seems to be nature's way for safeguarding the cell against outside electrical disturbances.

Working in this direction, Nordenstrom was led to develop a quite successful method for the cure of cancer by introducing electrodes to supply electric current directly inside the cancerous area. An electric contact in a small area creates a strong field, of the order of several volts per meter v/m, which is inversely proportional to the separation of the electrodes. Theoretically, this field can reach any value by reducing the separation distance of the contact electrodes and might be independent of the total potential in the separation. Thus, in practice, the field of the cellular membrane can be overcome by an invasive or contact method. Unfortunately, implantation of invasive electrodes involves surgery and creates the risk of infection at the implantation site. However, with prior art non-invasive techniques, it has been practically impossible to achieve these values for the electrical field without ionizing the atmospheric air and, therefore, a transfer of electrical charges or ions across the cellular membrane could not take place with fields which will not first break down the atmospheric air.

The use of static magnetic fields is known to have no significant influence of the static distributions of charges or ions within the cells. Also, a strong electrostatic field may produce an initial displacement of electrical charges, but cannot produce a substantial electric current, such as would be required for ion displacement and electrolytic transport. Moreover, the usual alternating sinusoidal electric field does not appear to have sensible results, due to the successive creation and removal of the electric charges, as well as because such an influence must be at least of the order of $10^6$ volts per meter for affecting a biologic cell membrane. Such a value is macroscopically prohibitive, since it surpasses the dielectric strength of air. The use of alternating sinusoidal magnetic fields causes an inductive electric voltage which is theoretically equal to the initial electric voltage of the source which alters the magnetic flux of the coil. However, if the magnetic coupling is less than 100%, which is always the case, the induced voltage will be smaller than the voltage of the source. For ion movement across the cellular membrane to occur, an initial source is required with a field greater than that of the transmembrane potential. However, as explained, this surpasses the dielectric strength of the air and has, therefore, been impossible with the devices of the prior art. The present invention overcomes this problem by instantaneously boosting the voltage to from one to one hundred times the dielectric value of air and quickly reducing the voltage to a safe value before ionization of the air can occur. By bombarding the semitransparent or semiconductive membrane of the cells by short duration burst of magnetic pulses caused by similar bursts of voltages, the transmembrane potential may be increased by ion conduction across the membrane. By bombarding the membrane of degenerate cells or bigger microorganisms with even stronger bursts of magnetic pulses caused by stronger bursts of voltage bursts, pressure inside the degenerate cell or bigger microorganism is increased. This pressure can burst or kill these degenerate cells or relatively bigger microorganisms of biological matter. Thus, this process can be used to perform cold pasteurization or to cause therapeutic changes in infected tissues or organs.

BRIEF SUMMARY AND OBJECTS OF INVENTION

The present method, in order to produce an electrical effect on the cellular membrane from afar, which will be substantial and feasible, uses plasma oscillations observed in electric discharges in various gases under pressure. During these oscillations, a significant energy increase is observed, for a percentage of the electron or ion flow in the arc, which far surpasses any potential difference in the discharge setup. The energy increase of these electrons or ions is achieved by a corresponding decrease in the energy of the remaining electrons or ions and results in the plasma being forced to oscillate with an eigenfrequency(ies) which is(are) characteristic of the gas plasma. This phenomenon was first observed by Langmuir in 1925 and was studied independently by the present inventor (P.T. Pappas, Proceedings, International Conference For Free Energy, Eisiedeln, Switzerland, 1989; International Tesla Symposium, Colorado Springs, 1990; 26th Intersociety Energy Conversion Engineering Conference, Boston, Mass., 1991). During the measurements of the inventor, an instantaneous increase of the effective voltage and current 10 to 100 times greater than the available potential and average current was observed along a simple circuit with an oscillating plasma of arc discharge. The ohmic resistance of the arc plasma is expected to be smaller than the total maximum value of the circuit, on the order of 0.5 Ohm, corresponding to the total measurable resistance of such networks. As a result, such a plasma arc is equivalent to a strongly varying resistance, from an infinite value before ignition to less than 0.5 Ohm after ignition, and subsequently to a negative value of the order of −100 Ohm. This variation is equivalent, theoretically, to a gain of infinity/0.5, which equals plus infinity, and to a subsequent negative gain of 0.5/−100<0, meaning that a significant excess of alternating electromotive voltage, alternating electric current and effective power is produced for a short period time in the circuit. The efficiency is incomparably better than any solid state technique known which exhibit only a small finite gain. The increase of said values is comparable to the time intervals of molecular vibrations and these time intervals are short and are not sufficient to produce atmospheric ionization or to produce general ionization. The source voltage is generally smaller than that required for ionizing air, and is increased substantially instantaneously by the plasma oscillations. This increase is sufficiently strong to cause ion transfer across the cellular membrane or across the membrane of microorganisms and cause pressure and potential increase. Moreover, the apparatus of the present invention is operated remotely and non-invasively, without any physical contact, and may even be applied over ordinary clothing. Moreover, the penetration depth for moderate power is adequate for most cases and is proportional to the intensity of the applied field which, theoretically, means that it can reach any desired depth by increasing the instantaneous power without ionizing the air. The present method is found to be effective to the same degree as microcontact, but avoids the disadvantages of electrode implantation and is not local, but can effective over large areas and depth. It also causes no ionization of the air because of the extremely short duty cycle.

Another unique property of the present method is obtained by the use of special plasma gases. As noted above, the frequency(ies) and characteristics of the plasma oscillations are dependent upon the particular gas elements of the plasma. Thus, by use of special gases, it is possible to produce the radio eigenfrequencies, which are absorbed through resonance by similar elements existing in biological matter. For instance, if nitrogen is contained in the gas plasma, it is possible to selectively excite the nitrogen atoms in the biological matter into oscillation. As a result, nitrogen atoms existing in the form of chemical compounds in a biologic area will selectively absorb this energy due to resonance of the nitrogen atoms in such compounds. This energy surplus in the biologic nitrogen atoms can provide the necessary energy to promote an endothermal chemical reaction and may allow the activated nitrogen atoms to move and participate in latent chemical reactions, which would not otherwise have occurred due to lack of available energy. Thus, it becomes possible to selectively initiate or catalyze a selected chemical reaction, while avoiding another reaction which could result from application of the same amount of energy of a less specific nature. As an example, if we consider two chemical compounds, XAB and Y, whereby the first compound, XAB, contains two chemical elements A and B which can be transferred to the Y compound by supplying appropriate energy. By supplying selected energy, we may selectively produce two alternative endothermic chemical reactions:

$$XAB+Y+\text{plasma energy } A = XA+YB \quad (1)$$

or $$XAB+Y+\text{plasma energy } B = XB+YA \quad (2)$$

Thus, with energy coming from plasma containing element A, we can activate chemical reaction (1), whereas with the energy coming from plasma containing element B, we can activate chemical reaction (2). Moreover, these reactions can be activated selectively and at will.

Accordingly, it is an object of the present invention to provide improved methods and apparatus for the therapeutic treatment of patients.

Another object of the present invention is to provide improved methods and apparatus for electrotherapeutic treatment of patients.

An additional object of the present invention is to provide improved methods and apparatus for treating patients with pulsed magnetic induction, with the resulting induced current and voltage.

A further object of the present invention is to provide improved methods and apparatus for treating patients with pulsed magnetic induction, with the resulting induced current and voltage without requiring implantation of electrodes.

Another object of the present invention is to provide improved methods and apparatus for treating patients with pulsed magnetic induction, which is non-invasive and may even be performed over ordinary clothing.

An additional object of the present invention is to provide improved methods and apparatus for electrotherapeutic treatment of patients which allows selective initiation or catalyzation of chemical reactions within a patient.

Yet another object of the present invention is to provide improved methods and apparatus for employing pulsed magnetic induction to induce electrical voltage and current within biological matter to produce therapeutic results.

A further object of the present invention is to provide improved methods and apparatus for overcoming the transmembrane potential of human cells without using excessive and ionizing the atmospheric air high voltages Another object of the present invention is to provide improved methods and apparatus for selectively stimulating one or more desired elements within a patient or biological matter.

A specific object of the present invention is to provide an improved method and apparatus for pulsed magnetic induction by creating a plasma, supplying energy to excite said plasma to oscillate at a higher amplitude than the amplitude of the supplied energy, and applying said the resulting oscillations to a patient or biological matter.

Another specific object of the present is to provide an improved method and apparatus for magnetic induction by creating a plasma containing a specific desired element, supplying energy to excite said element to oscillate at a characteristic radio eigenfrequency(ies), and applying said radio eigenfrequency(ies) to a patient to cause absorption of said energy by atoms of said specific element due to resonance.

An additional specific object of the present invention is to provide improved methods and apparatus for employing magnetic induction to induce electrical voltage and current within biological matter.

A further specific object of the present invention is to provide improved methods and apparatus for employing pulsed magnetic induction and the related induced electrical current and voltage to kill microorganisms or extinguish degenerate and/or weak cells.

These and other objects and features of the present invention will be apparent from the following detailed

DETAILED DESCRIPTION OF THE INVENTION

Figure 1:
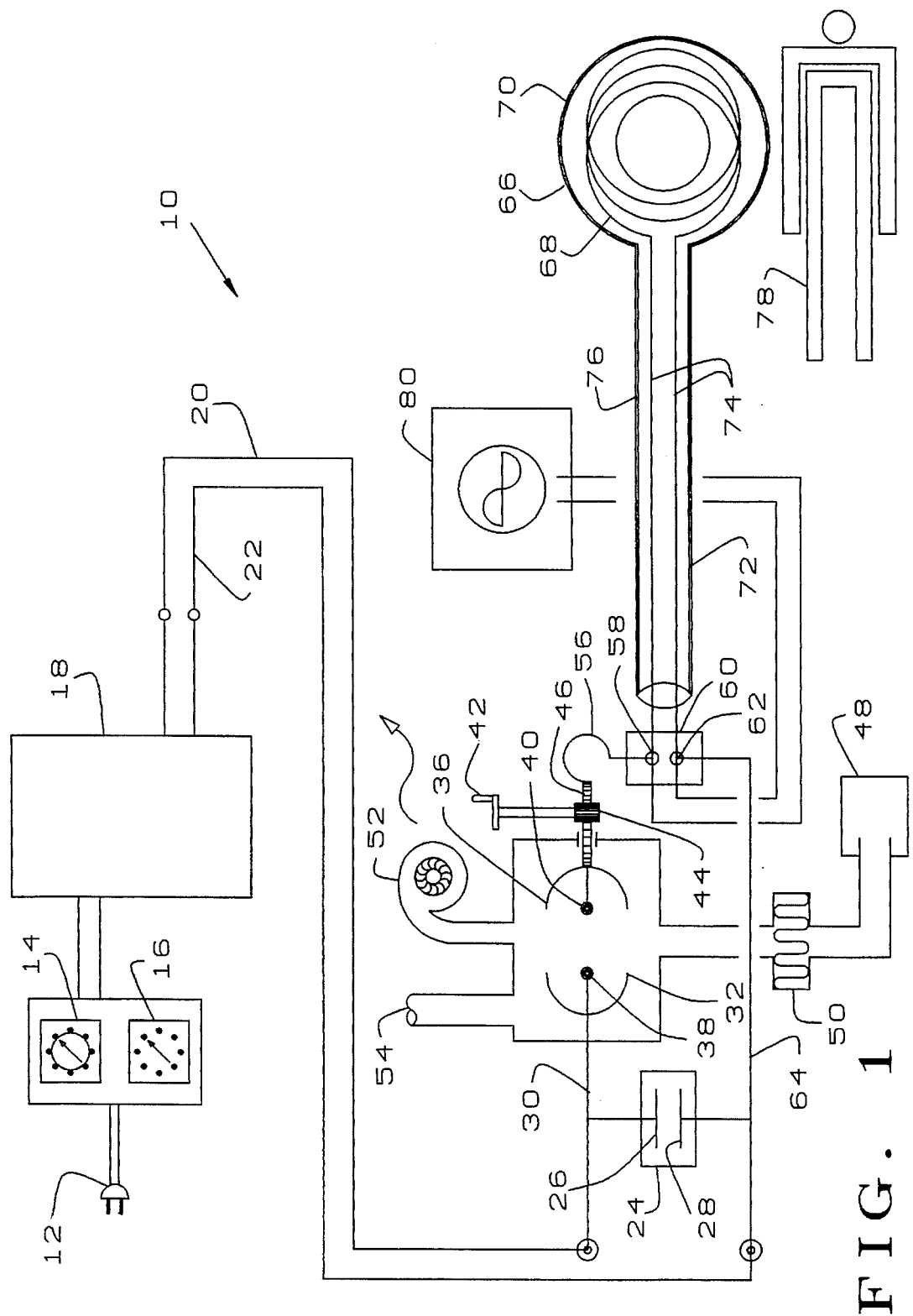
FIG. 1 is a diagrammatic representation of apparatus for performing pulsed magnetic induction in accordance with the method of the present invention.

In that form of the present invention chosen for purposes of illustration in the drawing, FIG. 1 shows a device, indicated generally at 10, having an electrical power receptor 12 for receiving alternating current electrical energy, at 220 volts and 50/60 Hz, and supplying the energy to a suitable timer switch 14, which regulates the operational period of the device 10. The switch 14 passes the electrical energy through a high-voltage variable transformer 16 to a rectifier 18, which converts the alternating current to a square wave at a frequency of only a few Hertz. The pulses of this square wave signal are sent through conductors 20 and 22 to charge a capacitive storage bank 24, which consists of two electrodes 26 and 28 and which is capable of storing a high potential marge and is capable of discharging substantially instantaneously. As the storage bank 24 is charged, the square waves supplied to electrode 26 of the storage bank 24 are also supplied, through conductor 30, to the anode 32 of plasma chamber 34. The plasma chamber 34 contains a pair of hemispherical electrodes, anode 32 and cathode 367 each having central probes 38 and 40, respectively. The spacing between the anode probe 38 of the anode 32 and probe 40 of the cathode 36 is adjustable by suitable means, such as crank 42, which actuates rack 44 and pinion 46 to vary the position of the cathode 36 and probe 40. Atmospheric air and gases, such as Nitrogen, Argon and the like are supplied to the plasma chamber 34 from one or more sources 48, through inlet filter 50 and are exhausted from the plasma chamber 34 by outlet fan 52. Also, a viewing window 54 is provided to allow the operator to observe the character of the plasma within the plasma chamber 34. The cathode 36 of the plasma chamber 34 is connected by a flexible high voltage line 56 to contact 58 of junction box 60. The other contact 62 of the junction box 60 is connected by conductor 64 to electrode 28 of the storage bank 24. An induction probe, indicated generally at 66, contains an induction coil 68, which is connected across the contacts 58 and 62 of the junction box 60 and which preferably has a diameter of 30 centimeters and is formed of approximately 2–10 turns of at copper wire having cross sectional area of at least 6 square millimeters, so as to provide very high rates of power, current >1000amps and voltage. The induction coil 68 is enclosed within a high insulation toroid 70, formed of suitable material, such as silicon, teflon or the like. As seen in FIG. 1, the induction probe 66 also has a tail portion 72, which contains the conductors 74 connecting the induction coil 68 to the junction box 60 encased within a sheath 76 formed of the same material as the toroid 70. The tail portion 72 serves to allow adjustable positioning of the induction coil 68 with respect to the patient, indicated generally at 78, and may be up to a few meters in length.

Finally, for test purposes or calibration, an oscilloscope 80 is connected across the electrodes 58 and 62 of the junction box 60 to provide a visual indication of the electrical signal being supplied to the induction probe 66 and, hence, to the patient 78.

Figure 2:
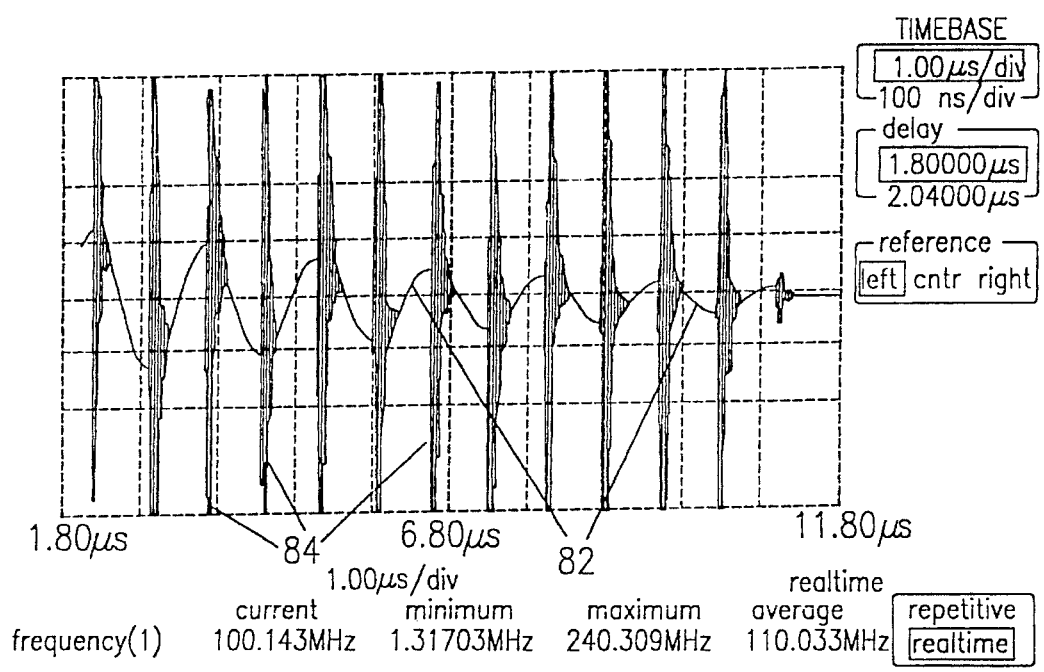
FIG. 2 is an oscillogram showing the oscillations produced in the output coil of the apparatus of FIG. 1.
Figure 3:
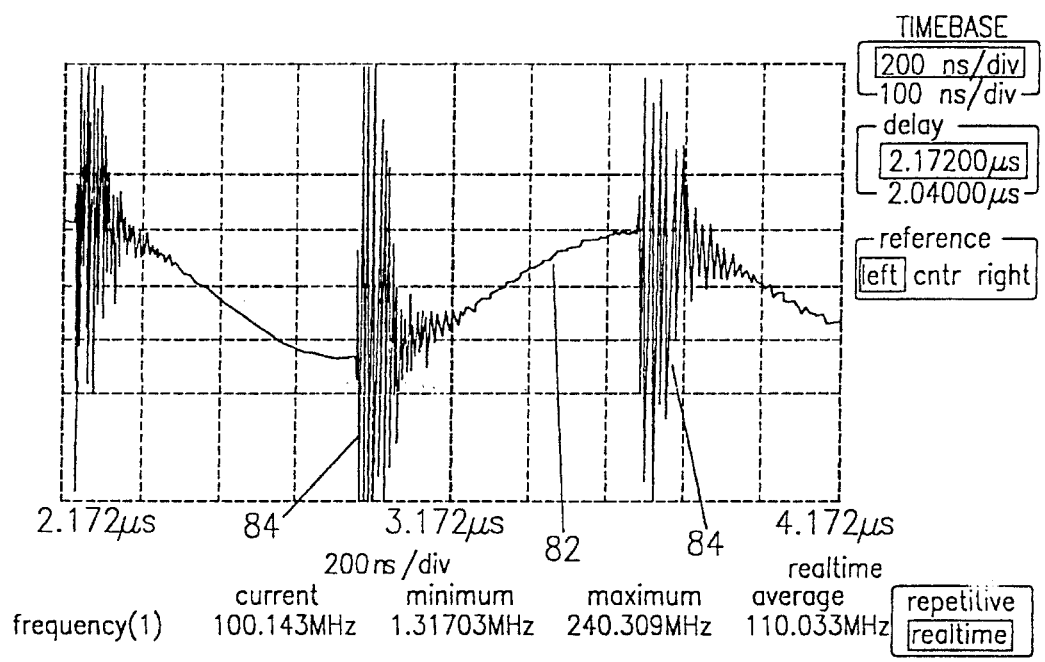
FIG. 3 is an enlarged oscillogram showing the characteristic radio eigenfrequency(ies) oscillations produced by the output coil of the apparatus of FIG. 1.

In use, the induction probe 66 is positioned to overlie a desired portion of the body of the patient 78 and rack 44 is rotated by crank 42 to move pinion 46 to provide a desired spacing between electrodes 32 and 36 for initiation of plasma ionization within the plasma chamber 34. Next, exhaust fan 52 is started and said gases are introduced into the plasma chamber 34 from gas source 48. An appropriate value is set for the variable transformer 16 and timer switch 14 is actuated to pass electrical energy from receptor 12 for a period of time, as selected by the timer switch 14. By watching through the viewing window 54, the observer can determine the operation condition of the device 10 and, if necessary or desirable, can adjust this by varying the spacing between the electrodes 32 and 36 of the plasma chamber 34. As seen in FIGS. 2 and 3, when the oscilloscope 80 is connected as shown, it will show a generally sinusoidal curve 82, indicative of the oscillations produced by the circuit composed of an inductance, resistance and capacitance, and will have bursts 84 occurring at the positive and negative peaks of the sine curve 82, caused by the eigen-oscillations of the selected gases, such as air or Nitrogen, and having an eigenfrequency(ies) which is characteristic of the selected gaseous elements. These energy bursts are substantially instantaneous and are of such short duration that they cannot serve to ionize the surrounding air. Moreover, the energy contained in these bursts penetrates into the body of the patient 78 and is selectively absorbed by those elements within cells of the patient 78 which resonate to the characteristic eigenfrequency(ies) caused by ionization of the selected gases from gas source 48. In prior art plasma techniques, similar energy burst have been observed. However, because the phenomena was not properly understood, steps have been taken to suppress the burst energy. As discussed above, this selective absorption serves to trigger selected chemical reactions within the cells of the patient 78 to produce desired therapeutic results. Thus, in accordance with the method of the present invention, enhancement of the burst energy is preferred. The energy supplied by the induction coil 68 will have a generally a low frequency damping sinusoidal base curve characteristic of the LCR circuit, having a duty cycle of the order of 0.001% with a series of about 10 to 15 equal (except the first one) bursts of radio eigenfrequency(ies) at each minimum or maximum of the low frequency cycle, having durations of less than $10^{-6}$ seconds each.

Obviously, numerous variations and modifications can be made without departing from the spirit of the present invention. Therefore, it should be clearly understood that the form of the present invention described above and shown in the figures of the accompanying drawing is illustrative only and is not intended to limit the scope of the present invention.

What is claimed is:

1. Apparatus for pulsed magnetic induction comprising:

means for creating a plasma containing at least one specific desired gaseous element, means for supplying energy to excite atoms of said gaseous element to oscillate at characteristic radio eigenfrequencies and magnetic frequencies, and means for inductively applying pulses of said radio eigenfrequencies and the magnetic frequencies produced to a target matter to cause selective absorption of energy by atoms of said specific element within said matter similar to the atoms of said specific element due to resonance.

2. The apparatus of claim wherein:
said means for creating a plasma comprises a plasma chamber containing a pair of selectably spaced electrode wherein said gaseous element is ionized.

3. The apparatus of claim 1 wherein:
said means for applying said radio eigen-frequencies to said target matter includes an induction probe.

4. The apparatus of claim 3 wherein:
said induction probe is formed to provide rates of power of magnetic pulses and to induce higher electrical current and to induce higher voltage into exposed matter without causing significant heating.

5. The apparatus of claim 3 wherein:
said induction probe contains an induction coil formed of at least one turn of wire made from a group of high conductive metals consisting of copper, gold, silver, and platinum, and the like, and having a diameter of at least 6 square millimeters to sustain a strong electrical current of at least 1000 amps.

6. The apparatus of claim 5 wherein:
said induction coil has a diameter at least a fraction of one centimeter.

7. The apparatus of claim 5 wherein:
said induction probe is encased within a shield formed of electrically insulating material.

8. The apparatus of claim 5 wherein:
said induction probe has a tail portion which allows adjustable positioning of said induction probe with respect to said target matter.

9. The apparatus of claim 1 wherein:
said means for producing a plasma produces energy having instantanious bursts of high frequency electrical energy having amplitudes which are higher than those of any other potential energy in said apparatus.

10. The apparatus of claim 1 wherein:
said means for supplying energy comprises a capacitive energy storage bank.

11. The apparatus of claim 1 further comprising: means for displaying characteristic of said plasma.

12. The apparatus of claim 1 wherein:
said means for creating a plasma includes a pair of concave electrodes arragned in facing relationship and each having a central probe projecting toward the other of said electrodes.

13. The apparatus of claim 12 wherein:
said electrodes are hemispherical.

14. The apparatus of claim 1 further comprising:
means for exciting said plasma to emit said radio eigen-frequencies in bursts having durations of about $10^{-4}$ to $10^{-6}$ seconds.

15. The apparatus of claim 1 wherein:
said means for supplying energy functions in an oscillating manner having a duty cycle of the order of 0.001 percent.

16. The apparatus of claim 1 wherein:
said means for supplying energy functions in an oscillating manner having a duty cycle of the order of 0.001 percent and causes said plasma to emit radio eigen frequencies in bursts having durations of less than $10^{-4}$ seconds.

17. A method for magnetic induction comprising the steps of:
creating a plasma containing at least one specific desired element, supplying energy to excite said element to oscillate at characteristic radio eigenfrequencies, and
applying said radio eigenfrequencies by magnetic induction to a patient to cause absorption of energy by atoms of said patient similar to atoms of said specific element due to resonance.

* * * * *